United States Patent [19]

Tomita et al.

[11] Patent Number: 4,892,882
[45] Date of Patent: Jan. 9, 1990

[54] CARBAMOYLOXY-ISOXAZOLE DERIVATIVES, THEIR PREPARATION AND INSECTICIDAL COMPOSITIONS CONTAINING THEM

[75] Inventors: Kazuo Tomita; Tadashi Murakami, both of Hiromachi; Hideakira Tsuji, Shiga; Keigo Matsumoto, Shiga; Katsuhiro Fujita, Shiga, all of Japan

[73] Assignee: Sankyo Company Limited, Tokyo, Japan

[21] Appl. No.: 692,869

[22] Filed: Jan. 18, 1985

Related U.S. Application Data

[60] Division of Ser. No. 527,180, Aug. 26, 1983, abandoned, which is a continuation of Ser. No. 318,602, Nov. 5, 1981, abandoned.

[30] Foreign Application Priority Data

Nov. 11, 1980 [JP] Japan .................. 55-158550

[51] Int. Cl.$^4$ .................. A01N 47/18; C07D 261/12
[52] U.S. Cl. ..................... 514/380; 548/243
[58] Field of Search ............... 548/240, 243; 514/380

[56] References Cited

U.S. PATENT DOCUMENTS

| | | | |
|---|---|---|---|
| 3,629,474 | 12/1971 | Ghosh et al. | 548/243 |
| 3,843,669 | 10/1974 | Punja et al. | 424/272 |
| 3,892,694 | 7/1955 | Kezerian | 544/157 |
| 4,067,922 | 1/1978 | Oswald et al. | 260/940 |
| 4,215,075 | 7/1980 | Magee | 260/464 |
| 4,579,860 | 4/1986 | Tomita et al. | 514/380 |

FOREIGN PATENT DOCUMENTS

| | | | |
|---|---|---|---|
| 257272 | 9/1967 | Austria | 424/272 |
| 823001 | 11/1951 | United Kingdom | 424/272 |
| 1245238 | 9/1971 | United Kingdom | 548/243 |

OTHER PUBLICATIONS

Wagner and Zook, "Synethetic Organic Chemistry", p. 484 (1955).
Jones and Jones, *Pests of Field Crops*, St. Martin's Press, New York (1974), pp. 4, 5, 12 and 380–382.

*Primary Examiner*—Donald G. Daus
*Attorney, Agent, or Firm*—Frishauf, Holtz, Goodman & Woodward

[57] ABSTRACT

Compounds of formula (I):

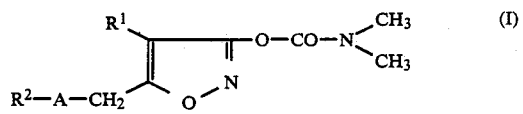

(wherein:
  $R^1$ represents a hydrogen atom or a halogen atom;
  $R^2$ represents a $C_1$–$C_6$ alkyl group; and
  A represents an oxygen atom, a sulphur atom, a sulphinyl group or a sulphonyl group)

have good insecticidal activity coupled with a low toxicity to warm-blooded animals. Compounds in which A represents an oxygen or sulphur atom can be prepared by reacting a corresponding alkali metal alkoxide or mercaptide with the corresponding 3-dimethylcarbamoyloxy-5-halomethylisoxazole derivative, while compounds where A represents a sulphinyl or sulphonyl group may be prepared by oxidizing the corresponding compound wherein A represents a sulphur atom. The compounds may be formulated with conventional insecticidal carriers or diluents and exhibit a synergistic increase in activity when combined with various known organic phosphate and carbamate insecticides.

16 Claims, No Drawings

CARBAMOYLOXY-ISOXAZOLE DERIVATIVES, THEIR PREPARATION AND INSECTICIDAL COMPOSITIONS CONTAINING THEM

BACKGROUND TO THE INVENTION

This application is a division of application Ser. No. 527,180, filed Aug. 26, 1983, which, in turn, is a continuation of Ser. No. 318,602 filed Nov. 5, 1981, both now abandoned.

The present invention relates to a series of new carbamoyloxyisoxazole derivatives, to processes for preparing them and to insecticidal compositions containing these new derivatives.

Insects cause considerable damage to plants and can represent a serious danger to health; at best, they are a major nuisance. Accordingly, large sums are spent on their destruction. Although many insecticides are available, a large number of these have to be used with considerable care, because they endanger the health of humans or other animals or because of their phytotoxicity. Moreover, because of their short life cycles, insects can develop immunity to many of the commonly used insecticides and, accordingly, there is always a continuing need for new compounds exhibiting insecticidal properties.

A number of compounds containing the isoxazole system are known to exhibit insecticidal activity. For example, Japanese Patent Publication No. 10145/70 discloses carbamoyloxyisoxazole derivatives of formula:

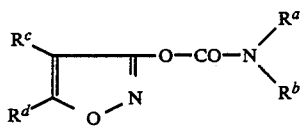

(in which $R^a$, $R^b$ and $R^d$ each represents a lower alkyl group and $R^c$ represents a hydrogen atom or a lower alkyl group) and discloses that these compounds are useful as insecticides. However, these compounds are potentially toxic to warm-blooded animals, which means that such severe restrictions would have to be placed upon their use that, in practice, they are unlikely ever to be actually used.

We have now discovered a series of carbamoyloxyisoxazole derivatives which, whilst chemically similar to the known compounds of the aforementioned Japanese Patent Application, surprisingly have very much reduced toxicity to warm-blooded animals but, at the same time, equally good or even better insecticidal activity.

BRIEF SUMMARY OF INVENTION

It is, therefore, an object of the invention to provide a series of new carbamoyloxyisoxazole derivatives having good insecticidal activity but weak toxicity to warm-blooded animals.

It is a further object of the invention to provide processes for the preparation of such derivatives.

It is a still further object of the invention to provide insecticidal compositions containing said derivatives as the active ingredient.

The compounds of the invention are those compounds of formula (I):

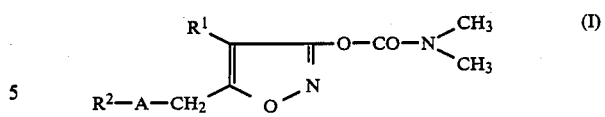

wherein:
$R^1$ represents a hydrogen atom or a halogen atom;
$R^2$ represents a $C_1$–$C_6$ alkyl group; and
A represents an oxygen atom, a sulphur atom, a sulphinyl group or a sulphonyl group.

The invention also provides a process for preparing these compounds, in which a compound of formula (III):

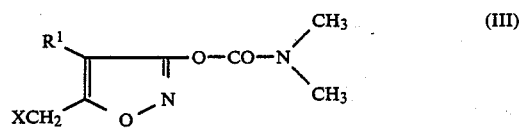

(wherein $R^1$ is as defined above and X represents a halogen atom) is reacted with an alkoxide or mercaptide of formula (IV):

$$R^2-A'-M \qquad (IV)$$

(in which $R^2$ is as defined above, A' represents an oxygen atom or a sulphur atom and M represents an alkali metal atom) to give a compound of formula (II):

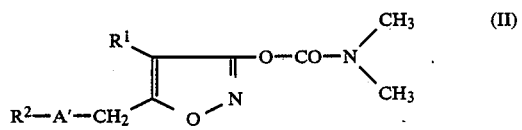

(in which $R^1$, $R^2$ and A' are as defined above) and optionally oxidizing said compound of formula (II) in which A' represents a sulphur atom to give a compound of formula (V):

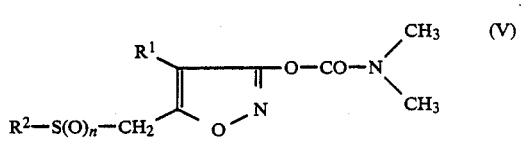

(wherein $R^1$ and $R^2$ are as defined above and n is 1 or 2).

The invention still further provides an insecticidal composition comprising an insecticide and a carrier or diluent, wherein the insecticide is one or more of the compounds of formula (I) defined above.

DETAILED DESCRIPTION OF INVENTION

In the compounds of formula (I), where $R^1$ represents a halogen atom, it may be a chlorine, bromine, iodine or fluorine atom and is preferably a chlorine, bromine or iodine atom, more preferably a chlorine or bromine atom. It is, however, preferred that $R^1$ should represent a hydrogen atom.

$R^2$ represents a straight or branched chain $C_1$–$C_6$ alkyl group, for example a methyl, ethyl, propyl, isopropyl, butyl, t-butyl or pentyl group, preferably a $C_1$–$C_3$ alkyl group and most preferably a methyl or ethyl group.

A preferably represents a sulphur atom.

Representative examples of compounds of the invention are listed below; the numbers appended to the compounds in the following list are used to identify those compounds hereinafter:

1. 3-Dimethylcarbamoyloxy-5-methylthiomethylisoxazole
2. 3-Dimethylcarbamoyloxy-5-ethylthiomethylisoxazole
3. 3-Dimethylcarbamoyloxy-5-propylthiomethylisoxazole
4. 3-Dimethylcarbamoyloxy-5-isopropylthiomethylisoxazole
5. 3-Dimethylcarbamoyloxy-5-methylsulphinylmethylisoxazole
6. 3-Dimethylcarbamoyloxy-5-ethylsulphinylmethylisoxazole
7. 3-Dimethylcarbamoyloxy-5-methylsulphonylmethylisoxazole
8. 3-Dimethylcarbamoyloxy-5-ethylsulphonylmethylisoxazole
9. 4-Chloro-3-dimethylcarbamoyloxy-5-methylthiomethylisoxazole
10. 4-Chloro-3-dimethylcarbamoyloxy-5-ethylthiomethylisoxazole
11. 4-Chloro-3-dimethylcarbamoyloxy-5-methylsulphinylmethylisoxazole
12. 4-Chloro-3-dimethylcarbamoyloxy-5-methylsulphonylmethylisoxazole
13. 4-Bromo-3-dimethylcarbamoyloxy-5-methylthiomethylisoxazole
14. 3-Dimethylcarbamoyloxy-4-iodo-5-methylthiomethylisoxazole
15. 3-Dimethylcarbamoyloxy-5-methoxymethylisoxazole
16. 3-Dimethylcarbamoyloxy-5-ethoxymethylisoxazole
17. 4-Chloro-3-dimethylcarbamoyloxy-5-methoxymethylisoxazole
18. 4-Chloro-3-dimethylcarbamoyloxy-5-ethoxymethylisoxazole.

Of the compounds listed above, particularly preferred compounds are Compounds No. 1, 2, 9 and 13.

Compounds of formula (II):

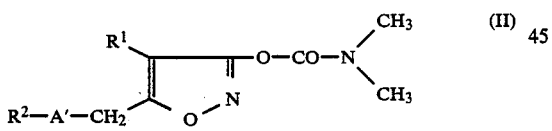

(in which $R^1$ and $R^2$ are as defined above and $A'$ represents an oxygen atom or a sulphur atom), that is to say compounds of formula (I) in which A is an oxygen or sulphur atom, may be prepared by reacting a compound of formula (III):

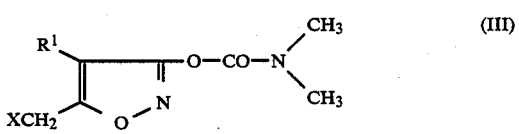

(in which $R^1$ and X are as defined above) with an alkoxide or mercaptide of formula (IV):

$$R^2—A'—M \qquad (IV)$$

(in which $R^2$, $A'$ and M are as defined above). The alkoxide or mercaptide may have been prepared in advance; alternatively, it may be prepared in situ in a suitable reaction solvent, by methods well-known in the art.

The reaction between the compounds of formulae (III) and (IV) is preferably effected in the presence of a solvent. Suitable solvents include: alcohols, such as methanol or ethanol; ethers, such as tetrahydrofuran, dioxan or diethylene glycol dimethyl ether; dimethylformamide; dimethyl sulphoxide; hexamethylphosphoric triamide; and mixtures of any two or more of these solvents. Of these solvents, ethers are particularly preferred. Where the compound of formula (IV) is a mercaptide, additional suitable solvents include: water; ketones, such as acetone or methyl isobutyl ketone; and mixtures of any two or more of the solvents. In the case of a mercaptide, methanol is the preferred solvent.

The reaction is preferably effected at a temperature greater than 0° C. but below the reflux temperature of the solvent used; preferably the temperature may range from above 0° C. to ambient temperature.

After completion of the reaction, the desired product of formula (II) may be separated and purified by techniques well-known in the art. For example, the solvent is distilled off under reduced pressure; the residue is diluted with a solvent such as methylene chloride; the organic solution is washed and dried; and, then the solvent is distilled off. The product may then be further purified, if desired, by recrystallization or by various chromatography techniques.

Compounds of formula (V):

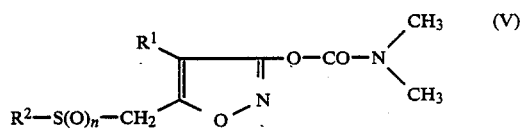

(wherein $R^1$ and $R^2$ are as defined above and n is 1 or 2), that is to say compounds of formula (I) in which A represents a sulphinyl or sulphonyl group, may be prepared by oxidizing the corresponding compound of formula (VI):

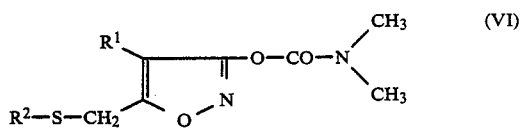

(in which $R^1$ and $R^2$ are as defined above); the compound of formula (VI) may itself have been prepared as described above.

The oxidizing agent is preferably a peroxide, for example hydrogen peroxide or an organic peroxide (such as benzoyl peroxide or m-chloroperbenzoic acid, preferably m-chloroperbenzoic acid).

Where hydrogen peroxide is employed as the oxidizing agent, the reaction is preferably effected in the presence of a solvent, for example an aliphatic carboxylic acid, particularly acetic acid, and the amount of hydrogen peroxide employed is preferably an approximately equimolar amount with respect to the compound of formula (VI). Where hydrogen peroxide is the oxidizing agent, the reaction is preferably effected at a temperature of from 5° C. to 25° C.

On the other hand, where an organic peroxide, particularly m-chloroperbenzoic acid, is used as the oxidizing agent, the reaction is also preferably effected in the presence of a solvent, the nature of which is not critical, provided that it has no adverse effect on the reaction; preferred solvents are halogenated hydrocarbons, such as methylene chloride, carbon tetrachloride, chloroform, chlorobenzene and o-dichlorobenzene. In this case, the organic peroxide is preferably employed in an amount greater than equimolar. The reaction will go to completion at a relatively low temperature, which may be below ambient temperature and as low as 0° C., within a few hours. However, the reaction can also be performed at the reflux temperature of the solvent employed. In the case where an organic peroxide is used, insolubles, if any, should be filtered off before the desired product is separated from the reaction mixture and purified.

After completion of the reaction, the solvent is preferably distilled off under reduced pressure, after which the residue is diluted with a solvent such as methylene chloride, the organic solution is washed and dried and then the solvent is distilled off. The resulting product may, if desired, be further purified by recrystallization or chromatography.

Compounds of formula (III) are novel and also form part of the present invention. They may be prepared by reacting a 3-hydroxyisoxazole derivative of formula (VII):

(in which $R^1$ and X are as defined above) with a carbamoyl halide of formula (VIII):

(in which Y represents a halogen atom).

The reaction is preferably effected in the presence of a solvent, the nature of which is not critical, provided that it has no adverse effect upon the reaction. Suitable solvents include: aliphatic and aromatic hydrocarbons, such as hexane, petroleum ether, benzene, toluene or xylene; chlorinated hydrocarbons, such as methylene chloride, chloroform or carbon tetrachloride; ethers, such as diethyl ether, diisopropyl ether, dioxan, tetrahydrofuran or diethylene glycol dimethyl ether; ketones, such as acetone, methyl ethyl ketone or methyl isobutyl ketone; and amides, such as dimethylformamide, diethylacetamide and hexamethylphosphoric triamide.

The temperature of the reaction may vary over a wide range and the reaction may, for example, be effected with ice-cooling or at temperatures up to ambient. The reagents are preferably employed in an equimolar or approximately equimolar ratio and the reaction is Preferably effected in the presence of an acid-binding agent, which may be organic (e.g. an organic amine, such as dicyclohexylamine, dimethylbenzylamine, picoline or lutidine) or inorganic (e.g. an alkali metal hydroxide, carbonate or bicarbonate, e.g. the hydroxide, carbonate or bicarbonate of sodium or potassium).

The compounds of formula (VII) which are used as starting materials in this process may be prepared, where $R^1$ represents a hydrogen atom, by the method described in Tetrahedron Letters 25, 2077 (1965). Compounds in which $R^1$ represents a halogen atom may be prepared by reacting the corresponding compound in which $R^1$ represents a hydrogen atom with a halogenating agent, for example chlorine, bromine, a sulphuryl halide or an N-halosuccinimide.

For example, compounds of formula (VII) in which $R^1$ represents a chlorine atom may be obtained by treating the corresponding compound in which $R^1$ represents a hydrogen atom with sulphuryl chloride, under reflux, in the presence or absence of an inert solvent, or with a calculated amount of gaseous chlorine, at ambient temperature, in dimethylformamide.

Compounds of formula (VII) in which $R^1$ represents a bromine or iodine atom may be obtained by treating the corresponding compound in which $R^1$ represents a hydrogen atom with N-bromosuccinimide or N-iodosuccinimide in dimethylformamide, with heating to about 60° C.

We have found that the compounds of formula (I) exhibit insecticidal activity against a wide variety of insect pests, including many of importance to agriculture, for example the green peach aphid, the green rice leafhopper and the brown planthopper; such activity is comparable with or even higher than that of known compounds but is accompanied by remarkably low toxicity to warm-blooded animals.

In order to control effectively harmful insects, the compounds of formula (I) may be formulated with carriers and diluents well-known in this art, particularly with agriculturally acceptable carriers and diluents, by conventional techniques. The resulting compositions may be in various forms, both solid and liquid and may be used for spraying or soil application to control insects on leaves and stems of various plants, including rice plants, fruit trees, vegetables and flowers. The compounds of the invention have the significant advantage of possessing systemic insecticidal activity.

The compounds of the present invention may be used in combination with various organic phosphate or carbamate insecticides in order to broaden the insecticidal spectrum and the compounds most suprisingly show synergistic activity in such combinations. Examples of insecticides which may be used in combination with the comounds of formula (I) include, for example:

O,O-Diethyl O-(5-phenyl-3-isoxazolyl)phosphorothioate (Isoxathion);

S-Methyl N-(methylcarbamoyloxy)thioacetimidate (Methomyl);

O,O-Dimethyl O-(3-methyl-4-nitrophenyl)thiophosphate (Fenitrothion);

O,O-Dimethyl O-[2-chloro-1-(2,4-dichlorophenyl)-vinyl]phosphate (Dimethylvinphos);

O,O-Dimethyl S-(α-ethoxycarbonylbenzyl)phosphorodithioate (Cidial);

O,O-Dipropyl O-4-methylthiophenylphosphate (Propaphos);

1-Naphthyl N-methylcarbamate (Carbaryl);

2-Isopropylphenyl N-methylcarbamate (Isoprocarb); and

3-Tolyl N-methylcarbamate (MTMC).

The synergistic effect obtained by combining one or more of the compounds of formula (I) with one or more organic phosphate or carbamate insecticides, such as those mentioned above, will be observed over a very wide range of ratios between the active ingredients. In general, however, we prefer to employ from 0.1 to 10 parts by weight of the organic phosphate or carbamate insecticide per one part by weight of the compound of formula (I).

The compounds of the invention may be employed in various types of preparation as is well-known for other insecticides; for example, they may be in the form of dusts, coarse dusts, micro granules, fine granules, wettable powders, emulsifiable concentrates, aqueous solutions or suspensions, water-soluble powders or oil suspensions. The carrier employed may be natural or synthetic and organic or inorganic; it is mixed with the active ingredient to assist that ingredient to reach the material to be treated, and to make it easier to store, transport or handle the active ingredient.

Suitable solid carriers include: inorganic substances, such as clays (examples of which are kaolinite, montmorillonite and attapulgite), talc, mica, pyrophyllite, pumice, vermiculite, gypsum, calcium carbonate, dolomite, diatomaceous earth, magnesium carbonate, apatite, zeolite, silicic anhydride and synthetic calcium silicate; organic substances derived from vegetables, such as soybean meal, tobacco powder, walnut powder, wheat flour, wood meal, starch and crystalline cellulose; synthetic or natural high molecular weight polymers, such as cumarone resins, petroleum resins, alkyd resins, polyvinyl chloride, polyalkylene glycols, ketone resins, ester gums, copal gum and dammar gum; waxes, such as carnauba wax and beeswax; or urea.

Examples of suitable liquid carriers include: paraffinic or naphthenic hydrocarbons, such as kerosine, mineral oil, spindle oil and white oil; aromatic hydrocarbons, such as benzene, toluene, xylene, ethylbenzene, cumene and methylnaphthalene; chlorinated hydrocarbons, such as carbon tetrachloride, chloroform, trichloroethylene, chlorobenzene and o-chlorotoluene; ethers, such as dioxan and tetrahydrofuran; ketones, such as acetone, methyl ethyl ketone, diisobutyl ketone, cyclohexanone, acetophenone and isophorone; esters, such as ethyl acetate, pentyl acetate, ethylene glycol acetate, diethylene glycol acetate, dibutyl maleate and diethyl succinate; alcohols, such as methanol, hexanol, ethylene glycol, diethylene glycol, cyclohexanol and benzyl alcohol; ether alcohols, such as ethylene glycol monoethyl ether, ethylene glycol monophenyl ether, diethylene glycol monoethyl ether and diethylene glycol monobutyl ether; other polar organic solvents, such as dimethylformamide or dimethyl sulphoxide; and water.

The insecticidal compositions of the present invention may contain surface active agents in order to emulsify, disperse, wet, spread, bind, control disintegration of, improve fluidity of or rust-proof the insecticidal composition or to stabilize the active ingredient; although any of the conventional classes of surface active agent, be they non-ionic, anionic, cationic or amphoteric, may be employed, we prefer to employ non-ionic and/or anionic surface active agents. Examples of suitable non-ionic surface active agents include: the polymerization adducts of ethylene oxide with higher alcohols, such as lauryl alcohol, stearyl alcohol or oleyl alcohol; the polymerization adducts of ethylene oxide with alkylphenols, such as isooctylphenol or nonylphenol; the polymerization adducts of ethylene oxide with alkylnaphthols, such as butylnaphthol or octylnaphthol; the polymerization adducts of ethylene oxide with higher fatty acids, such as palmitic acid, stearic acid or oleic acid; the polymerization adducts of ethylene oxide with mono- or di- alkylphosphoric acids, such as stearylphosphoric acid or dilaurylphosphoric acid; the polymerization adducts of ethylene oxide with amines, such as dodecylamine; the polymerization adducts of ethylene oxide with higher fatty acid amides, such as stearamide; the polymerization adducts of ethylene oxide with higher fatty acid esters of polyhydric alcohols, such as sorbitan, and the fatty acid esters themselves; and the polymerization adducts of ethylene oxide with propylene oxide. Examples of suitable anionic surface active agents include: alkyl sulphate salts, such as sodium lauryl sulphate or oleyl sulphate amine salt; alkyl sulphonate salts, such as sodium dioctyl sulphosuccinate or sodium 2-ethylhexene sulphonate; and aryl sulphonate salts, such as sodium isopropylnaphthalene sulphonate, sodium methylenebisnaphthalene sulphonate, sodium ligninsulphonate or sodium dodecylbenzene sulphonate.

Moreover, the insecticidal compositions of the present invention may be used in combination with high molecular weight compounds or other auxiliary agents, such as casein, gelatin, albumin, glue, sodium alginate, carboxymethylcellulose, methylcellulose, hydroxyethylcellulose or polyvinyl alcohol, in order to improve the properties and/or to increase the biological effect of the composition.

The above-mentioned carriers and various auxiliary agents may be used alone or in any desired combination, depending upon the type of preparation, the application and other factors.

The concentration of the active ingredient, the compound or compounds of formula (I), in the composition may vary over a wide range, although it will normally be from 0.1 to 95% by weight and more preferably from 1 to 90% by weight of the composition, depending upon the type of preparation.

For example, dusts may conveniently contain from 1 to 25% by weight of the active compound, the remainder being a solid carrier.

Wettable powders may conveniently contain, for example, from 25 to 90% by weight of the active compound, the remainder being a solid carrier and a dispersing and wetting agent, if required, together with a protective colloidal agent, a thixotropic agent and an antifoaming agent.

Granules may conveniently contain from 1 to 35% by weight of the active compound, a major portion of the remainder being a solid carrier. The active compound is preferably homogeneously admixed with the solid carrier or is adhered to or absorbed onto the carrier surface; the diameter of each granule is preferably from 0.2 to 1.5 mm.

Emulsifiable concentrates may conveniently contain, for example, from 5 to 50% by weight of the active compound and from 5 to 20% by weight of an emulsifying agent, the remainder being a liquid carrier, together with, if required, a corrosion inhibitor.

The invention is further illustrated by the following Examples, of which Examples 1 to 3 illustrate the preparation of certain starting materials for preparing the compounds of the invention, Examples 4 to 18 illustrate the preparation of compounds of the invention, Examples 19 to 22 illustrate insecticidal compositions containing the compounds of the invention and Examples 23 to 27 illustrate the use of the compounds and compositions of the invention in the control of insects.

EXAMPLE 1

4-Chloro-5-chloromethyl-3-hydroxyisoxazole

To a solution of 8.01 g of 5-chloromethyl-3-hydroxyisoxazole in 50 ml of benzene were added 10 g of sulphuryl chloride, and then the mixture was refluxed for 10 hours. At the end of this time, the solvent and the excess sulphuryl chloride were distilled off from the reaction mixture, and the residue was dissolved in 50 ml of diethyl ether and washed five times, each time with 20 ml of water. The washed diethyl ether solution was dried over anhydrous sodium sulphate, the solvent was removed by distillation, and the residue was extracted three times, each time with 30 ml of hot hexane. The hexane was distilled off from the extract and the residue was recrystallized from carbon tetrachloride, to give 4-chloro-5-chloromethyl-3-hydroxyisoxazole in the form of colourless crystals melting at 116°–118° C.

EXAMPLE 2

4-Bromo-5-chloromethyl-3-hydroxyisoxazole

To a solution of 1.33 g of 5-chloromethyl-3-hydroxyisoxazole in 2 ml of dimethylformamide were added 2.0 g of N-bromosuccinimide, and then the mixture was heated at 61° C. for 1.5 hours. The reaction mixture was then poured into 100 ml of ice-water and extracted with diethyl ether, after which the ethereal extract was dried over anhydrous sodium sulphate. The solvent was distilled off, leaving crystals, which were recrystallized from a mixture of diisopropyl ether and hexane, giving 4-bromo-5-chloromethyl-3-hydroxyisoxazole, in the form of white crystals melting at 136.5°–138° C. (with decomposition).

Following the same method, 5-chloromethyl-3-hydroxy-4-iodoisoxazole, melting at 147°–150° C. (with decomposition), was also prepared.

EXAMPLE 3

5-Chloromethyl-3-dimethylcarbamoyloxyisoxazole

To a solution of 2.0 g of 5-chloromethyl-3-hydroxyisoxazole in 60 ml of benzene were added 1.7 g of diemthylcarbamoyl chloride and 1.8 g of triethylenediamine (as acid-binding agent), and the mixture was stirred for 1 hour at ambient temperature. The reaction mixture was then washed twice, each time with 20 ml of water, after which the benzene solution was dried over anhydrous sodium sulphate. The solvent was then distilled off and the remaining oil was purified by column chromatography through silica gel eluted with a 10 : 1 by volume mixture of hexane and acetone, to give 5-chloromethyl-3-dimethylcarbamoyloxyisoxazole in the form of a faintly yellow oil, $n_D^{24.5} = 1.4977$.

Following the same procedure as described above, the following compounds were also prepared:
5-Chloromethyl-4-chloro-3-dimethylcarbamoyloxyisoxazole, $n_D^{23} = 1.5024$;
4-Bromo-5-chloromethyl-3-dimethylcarbamoyloxyisoxazole, $n_D^{25} = 1.5166$;
5-Chloromethyl-3-dimethylcarbamoyloxy-4-iodoisoxazole, melting at 69°–71° C.;
5-Bromomethyl-3-dimethylcarbamoyloxyisoxazole, $n_D^{23.5} = 1.5062$;
5-Bromomethyl-4-chloro-3-dimethylcarbamoyloxyisoxazole, $n_D^{22} = 1.5179$; and
4-Bromo-5-bromomethyl-3-dimethylcarbamoyloxyisoxazole, melting at 153°–154° C.

EXAMPLE 4

3-Dimethylcarbamoyloxy-5-methylthiomethylisoxazole

To 6 g of a 15% w/v aqueous solution of sodium methanethiolate, diluted with 20 ml of ethanol, was added, with stirring at room temperature, a solution of 3.07 g of 5-chloromethyl-3-dimethylcarbamoyloxyisoxazole in 5 ml of ethanol; stirring was continued for a further 30 minutes at room temperature.

The ethanol was then distilled from the reaction mixture and 20 ml of water were added to the residue. The mixture was extracted with 40 ml of methylene chloride, and the extract was dried over anhydrous sodium sulphate. The solvent was distilled off, leaving a brown oil, which was caused to crystallize by the addition of diisopropyl ether. The crystals were then recrystallized from diisopropyl ether, giving 2.62 g (yield 80.9%) of 3-dimethylcarbamoyloxy-5-methylthiomethylisoxazole, in the form of colourless crystals melting at 40°–41° C.

EXAMPLES 5 to 11

Following the procedures described in Example 4, the following compounds were prepared:
3-Dimethylcarbamoyloxy-5-ethylthiomethylisoxazole, melting at 49°–50° C.;
3-Dimethylcarbamoyloxy-5-propylthiomethylisoxazole, $n_D^{23} = 1.5078$;
3-Dimethylcarbamoyloxy-5-isopropylthiomethylisoxazole, $n_D^{23} = 1.5077$;
4-Chloro-3-dimethylcarbamoyloxy-5-methylthiomethylisoxazole, $n_D^{21} = 1.5221$;
4-Chloro-3-dimethylcarbamoyloxy-5-ethylthiomethylisoxazole, $n_D^{25} = 1.5162$;
4-Bromo-3-dimethylcarbamoyloxy-5-methylthiomethylisoxazole, $n_D^{24.5} = 1.5352$;
3-Dimethylcarbamoyloxy-4-iodo-5-methylthiomethylisoxazole, $n_D^{21} = 1.5563$.

EXAMPLE 12

The procedure described in Example 4 was repeated, except that sodium methoxide was used in place of the sodium methanethiolate, to give 3-dimethylcarbamoyloxy-5-methoxymethylisoxazole, $n_D^{24.5} = 1.4720$.

EXAMPLE 13

3-Dimethylcarbamoyloxy-5-methylsulphinylmethylisoxazole

A solution of 757 mg of 3-dimethylcarbamoyloxy-5-methylthiomethylisoxazole in 5 ml of methylene chloride was added dropwise over a period of 30 minutes, with stirring, to an ice-cooled solution of 711 mg of m-chloroperbenzoic acid in 15 ml of methylene chloride. The mixture was then stirred for a further 30 minutes, after which it was filtered and the precipitate was washed with 2 ml of methylene chloride. The filtrate and the washings were combined, and then the solvent was removed by distillation, leaving a colourless, crystalline residue, which was recrystallized from diethyl ether, to give 700 mg (yield 86.1%) of 3-dimethylcarbamoyloxy-5-methylsulphinylmethylisoxazole, in the form of colourless needles melting at 84°–85° C.

EXAMPLES 14 and 15

The procedure described in Example 4 was repeated, to prepare the following compounds:

3-Dimethylcarbamoyloxy-5-ethylsulphinylmethylisoxazole, melting at 85°–86° C.;
4-Chloro-3-dimethylcarbamoyloxy-5-methylsulphinylmethylisoxazole, melting at 79°–81° C.

EXAMPLES 16–18

The procedure described in Example 4 was repeated, except that the m-chloroperbenzoic acid was used in an amount of 2 moles per mole of starting isoxazole compound, to prepare the following compounds:
3-Dimethylcarbamoyloxy-5-methylsulphonylmethylisoxazole, melting at 145°–146° C.;
3-Dimethylcarbamoyloxy-5-ethylsulphonylmethylisoxazole, melting at 106°–107° C.;
4-Chloro-3-dimethylcarbamoyloxy-5-methylsulphonylmethylisoxazole, melting at 104°–105° C.

EXAMPLE 19

Dust 5 parts by weight of Compound No. 1, 50 parts by weight of talc and 45 parts by weight of kaolin were thoroughly blended to give a dust.

EXAMPLE 20

Wettable powder 50 parts by weight of Compound No. 2, 29 parts by weight of clay, 10 parts by weight of diatomaceous earth, 5 parts by weight of white carbon, 3 parts by weight of sodium ligninsulphonate, 2 parts by weight of Newcol 1106 ("Newcol" is a trade mark) and 1 part by weight of polyvinyl alcohol were thoroughly blended in a mixer and then pulverized three times with a hammer mill to give a wettable powder.

EXAMPLE 21

Granules 70 parts by weight of Compound No. 1 were finely pulverized, mixed with 30 parts by weight of clay and then blended in a mixer to make a premix. 10 parts by weight of the premix, 60 parts by weight of clay and 30 parts by weight of bentonite were thoroughly blended in a mixer and then a small amount of water was added to the mixture. The mixture was then compounded in a kneader, extruded through a screen whose apertures were of diameter 0.8 mm and then dried at 50° C. in a forced air oven. The dried compound was granulated with a sifter to give granules.

EXAMPLE 22

Emulsifiable concentrate 20 parts by weight of isoxathion, 5 parts by weight of Compound No. 1, 60 parts by weight of xylene and 15 parts by weight of Paracol PS ("Paracol" is a trade mark) were uniformly blended to give a emulsifiable concentrate.

EXAMPLE 23

Toxicity Test

Each of the compounds listed in Table 1 was administered in the form of a suspension, to which 0.5% w/v gum tragacanth had been added, to a group of 5 week old ddY-SLC series mice. Each test group consisted of 10 male and 10 female mice. The $LD_{50}$ value was calculated, by the method of Litchfield and Wilcoxon [J. Pharmac. Exp. Ther. 96, 99 (1949)], from the mortality rate after 7 days. The results are shown in Table 1.

TABLE 1

| Compound No. | $LD_{50}$ (mg/kg) | |
|---|---|---|
| 1 | male | 110.2 |
|   | female | 109.1 |
| 2 | male | 124.7 |
|   | female | 103.5 |
| 3-Dimethylcarbamoyloxy-5-methylisoxazole (Control) | male/female | 31.2 |

Similar tests were conducted with each of Compounds No. 3–15 and in each case, the $LD_{50}$ value was greater than 100 mg/kg. These results demonstrate the low toxicity of the compounds of the invention to warm-blooded animals.

EXAMPLE 24

Control of green peach aphid

Contact activity

A wettable powder was prepared by homogeneously mixing and pulverizing three times in a hammer mill 10 parts by weight of one of the test compounds indicated in Tables 2 and 3, 4 parts by weight of sodium dodecylbenzene sulphonate, 2 parts by weight of polyvinyl alcohol and 84 parts by weight of clay. The wettable powder thus prepared was then diluted with water to the concentration indicated in Table 1, and then 0.01% w/v of Gramin (a spreader) was added.

The resulting diluted solution was then sprayed onto the leaves of a cabbage bearing green peach aphids (*Myzus persicae*) in an amount of 10 ml per leaf. The leaf stalk of each leaf was then placed in a 30 ml bottle containing water and the mouth of the bottle was plugged with cotton wool. The bottles were then left in a room maintained at 25° C. After 72 hours, the percentage mortality of the aphids was assessed and the results are shown in Tables 2 and 3.

Systemic activity

Test suspensions were prepared as described above and then diluted to the concentrations indicated in Tables 2 and 3. The suspensions were then poured into 30 ml bottles. Leaves of the Chinese mustard "Komatsuna" bearing green peach aphids were then placed in the bottles and the mouths of the bottles were plugged with cotton wool. The bottles were placed in a room maintained at 25° C. for 72 hours, after which the percentage mortality of the aphids was assessed. The results are shown in Tables 2 and 3.

TABLE 2

| | Percentage mortality of green peach aphid | |
|---|---|---|
| Compound No. | Contact 50 ppm | Systemic 6.25 ppm |
| 1 | 100 | 100 |
| 2 | 100 | 100 |
| 3 | 86 | 100 |
| 4 | 81 | 96 |
| 5 | 86 | 100 |
| 6 | 88 | 100 |
| 7 | 82 | 85 |
| 8 | 80 | 85 |
| 9 | 100 | 100 |
| 10 | 97 | 100 |
| 11 | 100 | 100 |
| 12 | 82 | 90 |
| 13 | 100 | 100 |
| 14 | 86 | 100 |
| 15 | 84 | 100 |
| 3-Dimethylcarbamoyloxy-5- | 84 | 89 |

TABLE 2-continued

| Compound No. | Percentage mortality of green peach aphid | |
|---|---|---|
| | Contact 50 ppm | Systemic 6.25 ppm |
| methylisoxazole (Control) | | |

TABLE 3

| Compound No. | Percentage mortality of green peach aphid | |
|---|---|---|
| | Contact 12.5 ppm | Systemic 1.56 ppm |
| 1 | 83 | 100 |
| 9 | 90 | 100 |
| 13 | 99 | 100 |
| 3-Dimethylcarbamoyloxy-5-methylisoxazole (Control) | 34 | 74 |

EXAMPLE 25

Activity against the green rice leafhopper and the brown planthopper

A dust was prepared by homogeneously mixing and pulverizing twice with a pulverizer 2 parts by weight of each in turn of the test compounds indicated in Table 4 and 98 parts by weight of clay. The dusts were then sprayed onto rice seedlings planted in plastic pots and covered with a plastic cylinder in amounts sufficient to provide 10 mg of the 10% dust per pot (corresponding to 1.4 kg of dust per 10 ares). 10–15 of the final instar larvae of the green rice leafhopper (*Naphotettix cincticeps*) or of the brown planthopper (*Nilaparvata lugens*) of strains known to be resistant both to conventional organic phosphorus and carbamate insecticides were released into each pot. After maintaining the pots at 25° C. for 72 hours, the percentage mortality of the larvae was assessed. Each test was carried out twice and the results averaged. The results are shown in Table 4.

TABLE 4

| Compound No. | Percentage mortality | |
|---|---|---|
| | Green rice leafhopper | Brown planthopper |
| 1 | 65 | 100 |
| 2 | 67 | 95 |
| 3 | 68 | 68 |
| 9 | — | 100 |
| 3-Dimethylcarbamoyloxy-5-methylisoxazole (Control) | 9 | 22 |

EXAMPLE 26

Activity against the brown planthopper (mixed formulation)

Soil and water were placed into plastic pots having inside diameters and heights each of about 10 cm to prepare the pots for submerged cultivation, with water to a depth of about 2 cm. Rice seedlings were then planted in the pots and maintained in a greenhouse, until they had grown to a height of about 15 cm.

Dusts were prepared, each containing 0.1% w/w of Compound No. 1 or of the known organic phosphate or carbamate insecticides listed in Table 5, and these were homogeneously applied, in the amounts specified in the Table, to each pot. 10–15 of the final instar larvae of the brown planthopper were then released onto each pot. The pots were then covered and maintained at 25° C. for 72 hours, after which the percentage mortality of the larvae was assessed. The results are shown in Table 5.

The experiments were conducted using the known organic phosphate and carbamate insecticides either alone or together with Compound No. 1 (50 mg). The percentage mortality achieved using Compound No. 1 alone in an amount of 50 mg was also assessed and found to be 0%. The expected percentage mortality of the combination of Compound No. 1 with the known organic phosphate and carbamate insecticides was calculated by the method of C. I. Bliss [Ann. Appl. Biol. 26, 585 (1939)] and is shown in parentheses in the Table.

TABLE 5

| Species and Amount of organic phosphate or carbamate insecticide | Compound 1 0.1% dust | |
|---|---|---|
| | 0 mg | 50 mg |
| Dimethylvinphos 0.1% dust 100 mg | 14.7 | (14.7) 54.1 |
| MEP 0.1% dust 100 mg | 37.1 | (37.1) 75.8 |
| NAC 0.1% dust 50 mg | 29.2 | (29.2) 65.4 |
| MIPC 0.1% dust 50 mg | 25.0 | (25.0) 58.3 |
| MTMC 0.1% dust 50 mg | 20.8 | (20.8) 77.8 |

EXAMPLE 27

Activity against green peach aphids (mixed formulation)

Emulsifiable concentrates containing a total of 25% by weight of active ingredient or ingredients were prepared as described in Example 22 and diluted with water to the concentrations given in the following Table 6. Each emulsion contained as active ingredient Compound No. 1, Compound No. 9 or the known insecticide isoxathion alone or contained a mixture of isoxathion and Compound No. 1 or No. 9. The diluted emulsions were sprayed, in an amount of 10 ml per leaf, onto the leaves of the Chinese mustard "Komatsuna" bearing green peach aphids of a strain known to be resistant to organic phosphate insecticides. The leaf stalks of the leaves were placed into 30 ml bottles and the mouths of the bottles were plugged with cotton wool. After maintaining the leaves at 25° C. for 72 hours, the percentage mortality was assessed and the results are shown in Table 6. The expected percentage mortality of the combinations of Compound No. 1 or No. 9 with Isoxation is shown in parentheses in the table.

TABLE 6

| Concentration (ppm) of active ingredient | | | Percentage mortality |
|---|---|---|---|
| Compound 1 | Compound 9 | Isoxathion | |
| 0 | 0 | 25 | 0 |
| 0 | 0 | 50 | 4.4 |
| 5 | 0 | 0 | 25.8 |
| 10 | 0 | 0 | 59.8 |
| 0 | 2.5 | 0 | 20.1 |
| 0 | 5 | 0 | 38.4 |
| 5 | 0 | 25 | 98.9 (25.8) |
| 10 | 0 | 50 | 100 (61.6) |
| 0 | 2.5 | 12.5 | 95.4 (<20.1) |
| 0 | 5 | 25 | 100 (38.4) |

The results of the experiments carried out in Examples 26 and 27 illustrate the significant and unexpected synergy achieved when the compounds of the invention are used in combination with known organic phosphate and carbamate insecticides.

We claim:

1. An insecticidal composition comprising at least one insecticide and a carrier or diluent, wherein the insecticide is at least one compound of formula (I):

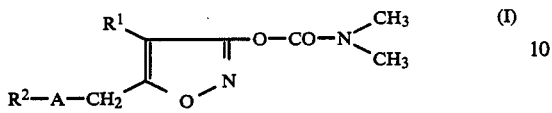

wherein:
R¹ represents a hydrogen atom or a bromine or chlorine atom;
R² represents a C₁–C₃, n-alkyl group; and
A represents a sulphur atom.

2. A composition as claimed in claim 1, wherein R² represents a methyl or ethyl group.

3. A composition as claimed in claim 1, wherein:
R¹ represents a hydrogen atom;
R² represents a methyl or ethyl group; and
A represents a sulphur atom.

4. A composition as claimed in claim 1, wherein said insecticide is selected from the group consisting of:
3-Dimethylcarbamoyloxy-5-methylthiomethylisoxazole
3-Dimethylcarbamoyloxy-5-ethylthiomethylisoxazole
4-Chloro-3-dimethylcarbamoyloxy-5-methylthiomethylisoxazole and
4-Bromo-3-dimethylcarbamoyloxy-5-methylthiomethylisoxazole.

5. The composition of claim 1 wherein said insecticide is 3-dimethylcarbamoyloxy-5-methylthiomethylisoxazole.

6. The composition of claim 1 wherein said insecticide is 3-dimethylcarbamoyloxy-5-ethylthiomethylisoxazole.

7. The composition of claim 1 wherein said insecticide is 4-chloro-3-dimethylcarbamoyloxy-5-methylthiomethylisoxazole.

8. The composition of claim 1 wherein said insecticide is 4-bromo-3-dimethylcarbamoyloxy-5-methylthiomethylisoxazole.

9. A compound of the formula (I)

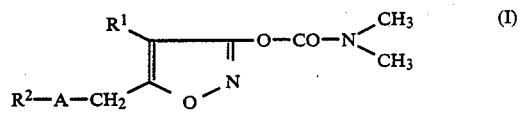

wherein:
R¹ represents a hydrogen atom or a bromine or chlorine atom;
R² represents a C₁–C₃ n-alkyl group; and
A represents a sulphur atom.

10. The compound of claim 9, wherein R² represents a methyl or ethyl group.

11. The compound of claim 9, wherein:
R¹ represents a hydrogen atom;
R² represents a methyl or ethyl group; and
A represents a sulphur atom.

12. The compound of claim 9, wherein said compound of the formula (I) is selected from the group consisting of:
3-dimethylcarbamoyloxy-5-methylthiomethylisoxazole
3-dimethylcarbamoyloxy-5-ethylthiomethylisoxazole
4-chloro-3-dimethylcarbamoyloxy-5-methylthiomethylisoxazole
4-bromo-3-dimethylcarbamoyloxy-5-methylthiomethylisoxazole.

13. The compound of claim 9, wherein said compound of the formula (I) is 3-dimethylcarbamoyloxy-5-methylthiomethylisoxazole.

14. The compound of claim 9, wherein said compound of the formula (I) is 3-dimethylcarbamoyloxy-5-ethylthiomethylisoxazole.

15. The compound of claim 9, wherein said compound of the formula (I) is 4-chloro-3-dimethylcarbamoyloxy-5-methylthiomethylisoxazole.

16. The compound of claim 9, wherein said compound of the formula (I) is 4-bromo-3-dimethylcarbamoyloxy-5-methylthiomethylisoxazole.

* * * * *

UNITED STATES PATENT AND TRADEMARK OFFICE
CERTIFICATE OF CORRECTION

PATENT NO. : 4,892,882

DATED : January 9, 1990

INVENTOR(S) : TOMITA et al

It is certified that error appears in the above-identified patent and that said Letters Patent is hereby corrected as shown below:

Title page, Section [56] References Cited, insert the following under "OTHER PUBLICATIONS":

Drabek et al, "Insecticidal N-acetylcarbamates", Chem. Abst. 77: 101164(b) (1972).

Kezerian, "Substituted Phosphorus-containing Alkylthiomethyl Carboxylates", Chem. Abst. 78: 15541(m) (1972).

Konecny, "Insecticidal N-methyl-O-[2-(methylthiomethyl)-alkoxyphenyl] carbamates", Chem. Abst. 78: 159289(h) (1973).

Signed and Sealed this

Fifteenth Day of December, 1992

Attest:

DOUGLAS B. COMER

*Attesting Officer*     *Acting Commissioner of Patents and Trademarks*